United States Patent [19]
Newman

[11] Patent Number: 6,035,704
[45] Date of Patent: Mar. 14, 2000

[54] APPARATUS FOR THE ENHANCEMENT OF WATER QUALITY IN A SUBTERRANEAN PRESSURIZED WATER DISTRIBUTION SYSTEM

[76] Inventor: Michael R. Newman, 741 5th St. NW., Naples, Fla. 34120

[21] Appl. No.: 09/096,626

[22] Filed: Jun. 12, 1998

[51] Int. Cl.[7] .................................................. E03B 7/00
[52] U.S. Cl. ......................... 73/61.41; 73/53.01; 137/236
[58] Field of Search ............................. 73/61.41, 863.01, 73/863.21, 863.71, 863.72, 168; 137/236, 624.14, 624.2; 210/170, 747, 143, 103, 92; 405/128, 52; 239/69, 70

[56] References Cited

U.S. PATENT DOCUMENTS

| | | | |
|---|---|---|---|
| 2,752,307 | 6/1956 | Baran et al. | 204/195 |
| 3,592,212 | 7/1971 | Schleimer | 137/93 |
| 4,483,189 | 11/1984 | Seal | 73/155 |
| 4,639,718 | 1/1987 | Gasper | 340/603 |
| 4,838,485 | 6/1989 | Rinkewich | 239/70 |
| 4,876,530 | 10/1989 | Hill et al. | 73/49.1 |
| 4,898,107 | 2/1990 | Dickinson | 110/346 |
| 5,011,598 | 4/1991 | Nathanson | 210/136 |
| 5,249,745 | 10/1993 | Berlotti | 137/624.14 |
| 5,261,348 | 11/1993 | Niehaus et al. | 166/64 |
| 5,264,368 | 11/1993 | Clarke et al. | 73/61.48 |
| 5,324,665 | 6/1994 | Lessard | 436/55 |
| 5,332,494 | 7/1994 | Eden et al. | 210/96.1 |
| 5,479,338 | 12/1995 | Ericksen et al. | 137/624.2 |
| 5,480,562 | 1/1996 | Lemelson | 210/745 |
| 5,490,561 | 2/1996 | Cardoso-Neto et al. | 166/264 |
| 5,527,470 | 6/1996 | Suda | 210/739 |
| 5,540,845 | 7/1996 | Blanchard et al. | 210/709 |
| 5,587,055 | 12/1996 | Hartman et al. | 203/1 |

*Primary Examiner*—Hezron Williams
*Attorney, Agent, or Firm*—Quarles & Brady LLP

[57] ABSTRACT

A self-contained water quality enhancement apparatus is provided for purging a low flow area of a subterranean water distribution system. The apparatus include: a water carrier system for transporting water through the apparatus, a flow control valve for adjusting the flow rate of water through the system; a programmable solenoid controller for activating and deactivating the flow control valve; electronic and/or optical sensing devices for measuring water quality; a data access and programming port; and an electronic control system. The components cooperate to provide a means for automatically measuring water quality and then purging water from the low flow area as required.

15 Claims, 4 Drawing Sheets

APPARATUS FOR THE ENHANCEMENT OF WATER QUALITY IN A SUBTERRANEAN PRESSURIZED WATER DISTRIBUTION SYSTEM

FIELD OF THE INVENTION

The invention relates in general to water quality maintenance devices and more particularly to a water sampling and purging apparatus for automatically maintaining water quality in a low flow area of an underground water distribution system.

BACKGROUND OF THE INVENTION

Traditional underground water distribution systems for residential and commercial areas often incorporate low flow or dead end portions by design. For instance, fire protection and land development codes often require oversized water mains for anticipated fire control and peak water demands. Such design features, although in the best interest of the community, have the effect of dramatically reducing water flow velocity and increasing water retention time within the water distribution system. The problem is further exacerbated by water distribution systems that experience large seasonal fluctuations in demand. These systems often experience additional reduction in water flow during non-seasonal periods of the year.

Low water flow conditions and corresponding increases in water retention time within portions of the water distribution system have the potential to degrade the chemical and microbiological quality of water transported through the distribution system. Degradation in water quality results from prolonged exposure to water system materials, internal sedimentation, and/or contaminant deposits within the piping system. Disinfectants are commonly used in an effort to control bacterial growth. However, as disinfectant residuals dissipate bacterial regrowth occurs.

The Federal Safe Drinking Water Act requires that potable, or drinkable, water systems maintain minimum disinfection residual levels, to prevent the regrowth of bacteria. In fact, mandatory testing programs have been enacted to track compliance and identify potential health hazards. Water systems failing to adhere to regulatory or operational water quality standards are subject to regulatory enforcement action, public disclosure of health hazards, and increased public and regulatory scrutiny.

Corrosion rates in low flow and stagnant areas can escalate as chemical reactions and microbiological activity increase. Corrosive water tends to dissolve certain materials commonly used in the construction of water distribution systems. The two primary metals of concern are iron and lead. Iron is commonly found in piping system materials. Lead is commonly found in older water systems that have incorporated lead joints, lead composite pipes and/or brass fittings. Elevated iron concentrations can result in violations of drinking water standards. In both potable and non-potable water distribution systems, excessive concentrations of iron can result in staining of structure surfaces, fixtures and clothing.

Bacterial hazards also abound in low flow or dead end portions of water distribution systems. Increased bacterial concentrations result from reductions in disinfection residuals which retard or prevent the regrowth of such bacteria. Maintenance of adequate water system disinfection residuals is necessary to afford protection from accidental or intentional introduction of microbiological contaminants into the distribution system. Microbiological films, referred to in the art as bio-films, can form on water distribution system components where adequate disinfectant residual levels are not maintained. Removal of such films is expensive and time consuming.

Historically, water distribution system compliance with water quality regulatory standards has been evaluated through the collection of water samples. Presently, samples are collected from private plumbing systems and stationary water sampling stations installed along the water system distribution system. These designated sampling locations often produce test results that are either inaccurate or not representative of water quality throughout the water distribution system.

Historically, the primary means of addressing water quality degradation in low flow or dead end areas has been to dispatch workers, on a complaint-by-complaint basis, to manually purge the water from a problem area of the system. This method does not provide an adequate solution, since its success is contingent on financial and human resource availability.

Another approach that has been employed to supplement manual flushing operations, has been the use of increased concentrations of disinfectant residuals, in an attempt to counteract the effects of disinfectant residual dissipation, which is a time dependent function of chemical and biological reactions. Using this approach, the disinfectant residual level of the entire system is increased or, alternatively, disinfectant booster stations are positioned at strategic areas along the water distribution system. However, due to suspicions that chlorine and other water-disinfecting chemicals may be carcinogenic, or responsible for creating carcinogenic substances during the disinfection process, there is a general consensus that dosage rates must be minimized. For instance, the Federal Safe Drinking Water Act is expected to establish a maximum limit of 4 mg/l for chlorine.

This prior art does not provide an adequate solution for addressing the aforementioned water quality degradation problems common at low flow and dead end areas of water distribution systems. The need for an adequate solution has been heightened as a result of an increase in the occurrence of known and suspected carcinogens in water distribution systems.

Accordingly, what is needed is an apparatus capable of analyzing water quality and purging low quality water from low flow or dead end areas of water distribution systems. In some cases, It would be desirable for the aforementioned apparatus to have an internal control system capable of automatically monitoring water quality and, subsequently, purging low-quality water from the low flow area based upon user defined water quality limits. In some cases, it would be further desirable for the analytical and purging function of the apparatus to be controllable by a remotely operated device.

SUMMARY OF THE INVENTION

The present invention provides an efficient and cost-effective means for maintaining water quality in low flow or dead end areas of an underground water distribution system. The invention generally embodies an apparatus for the automated analysis of water samples and purging of low quality water from such areas on an as-need basis. The apparatus greatly reduces present human resource requirements associated with performing these functions.

The apparatus is adapted for mounting above and below grade level, housing both above- and below-ground components. The major below-ground components of the apparatus include: a water inlet for introducing water from the water distribution system into the apparatus; a water carrier system for transporting water through the apparatus; an isolation valve for controlling the introduction of water into the apparatus; a flow control valve for controlling the flow of water through the apparatus; a water quality monitoring system; and an electronic control system for activating, monitoring, and deactivating sampling and purging functions of the apparatus. Various optional components are also contemplated. For instance, radio and/or telephonic telemetry equipment may be housed in the below-ground portion of the apparatus for remote activation and deactivation of the apparatus.

The major above-ground components of the apparatus include: a water purging portion; a programming/data transmission access port; electrical/optical sensing devices; an external water quality sampling adapter; and a power source. The programming access port receives operational instructions from a remotely-held programming device. Various optional components are also contemplated. For instance, a turbine generator may be housed in the above-ground portion of the apparatus for recharging the power source.

Generally, instructions are communicated from a hand held remote control device, through the programming access port, to a programmable solenoid controller which is a subcomponent of the electronic control system. Preferably, the solenoid controller has date and time function capabilities such that a remote operator can program the apparatus to perform water purging functions at programmed times. The programmable solenoid also communicates with chemical, electronic and/or optical sensing devices, providing a means for purging based upon water quality parameters. Preferably, the power source comprises a rechargeable battery. The system is housed in a water tight housing to prevent damage to internal components. The housing is specially designed to allow easy access to internal components. Bulky system components are stored below grade level in a specially designed water tight compartment, leaving only the relatively small aesthetically engineered portion of the housing above grade level.

DETAILED DESCRIPTION OF PREFERRED EMBODIMENTS

Figure 1:
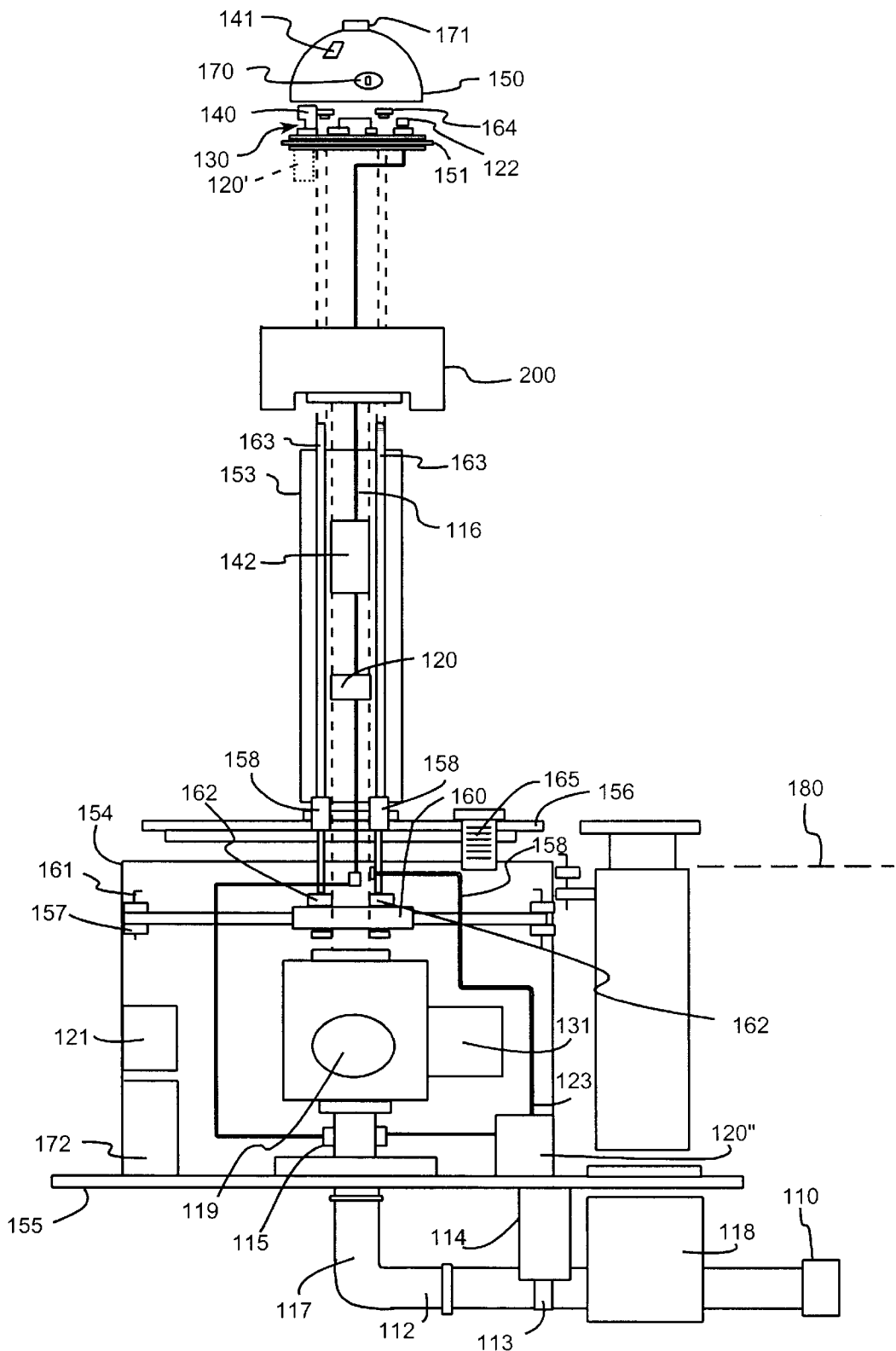
FIG. 1 is an elevation view, partially in cross section, of an apparatus in accordance with the present invention.

While the specification concludes with claims defining the features of the invention that are regarded as novel, it is believed that the invention will be better understood from a consideration of the following description in conjunction with the drawing figures, in which like reference numerals are carried forward.

Referring to FIG. 1, a multicomponent apparatus is provided for measuring the water quality of a subterranean water distribution system and selectively purging water therefrom. The apparatus is adapted for above and below ground, or grade level 180, mounting. As used herein, the term "upper portion" denotes structure located above grade level 180, and the term "lower portion" denotes structure located below grade level 180. In the preferred embodiment, the major components of the apparatus include: a housing; water transport apparatus; a programmable solenoid controller; a programming/data retrieval port; an electronic data control system; chemical, electronic and/or optical sensing devices; and a power source. Additionally, the apparatus may include a telephone and/or radio telemetry interface control system. The major system components are each comprised of subsystem components which cooperate to provide the advantages of the present invention.

Initially, water from a water distribution system (not shown) is received into water carrier piping 112 through water inlet 110. The dimensions and configuration of water inlet 110 are adapted for connection to the particular water distribution system piping. Water carrier piping 112 is made up of individual pipe segments. Water inlet 110 is connected to isolation valve 118. Isolation valve 118 controls the introduction of water into the apparatus. Under certain circumstances, it may be desirable to cut off water flow to the apparatus. For instance, isolation may be desirable when the apparatus is undergoing repair. Furthermore, in subfreezing climates, the isolation valve may be closed to isolate water from internal components, to prevent component damage from the expansion of freezing water. Carrier pipe 112 connects isolation valve 118 and carrier pipe elbow 117. Carrier pipe elbow 117 transitions the carrier pipe from a horizontal to vertical direction. The carrier piping extends through a gasketed opening in lower housing support platform 155 and connects to water flow control valve 119.

Flow control valve 119 varies water flow through the apparatus, thereby controlling the corresponding rate at which water is purged. In contrast to the manual methods of the prior art, the flow control valve of the present invention enables the discharge, or purging, of water at a controlled rate of flow over an extended period of time. As a result, the potential for land damage from erosion and flooding is greatly reduced. Reduced flow rates and longer activation times also promote conservation of water resources by maximizing percolation back into the surrounding area and minimizing water loss due to runoff. Carrier pipe 112 extends upwards from flow control valve 119, terminating at water flow dissipator 200.

Figure 2A:
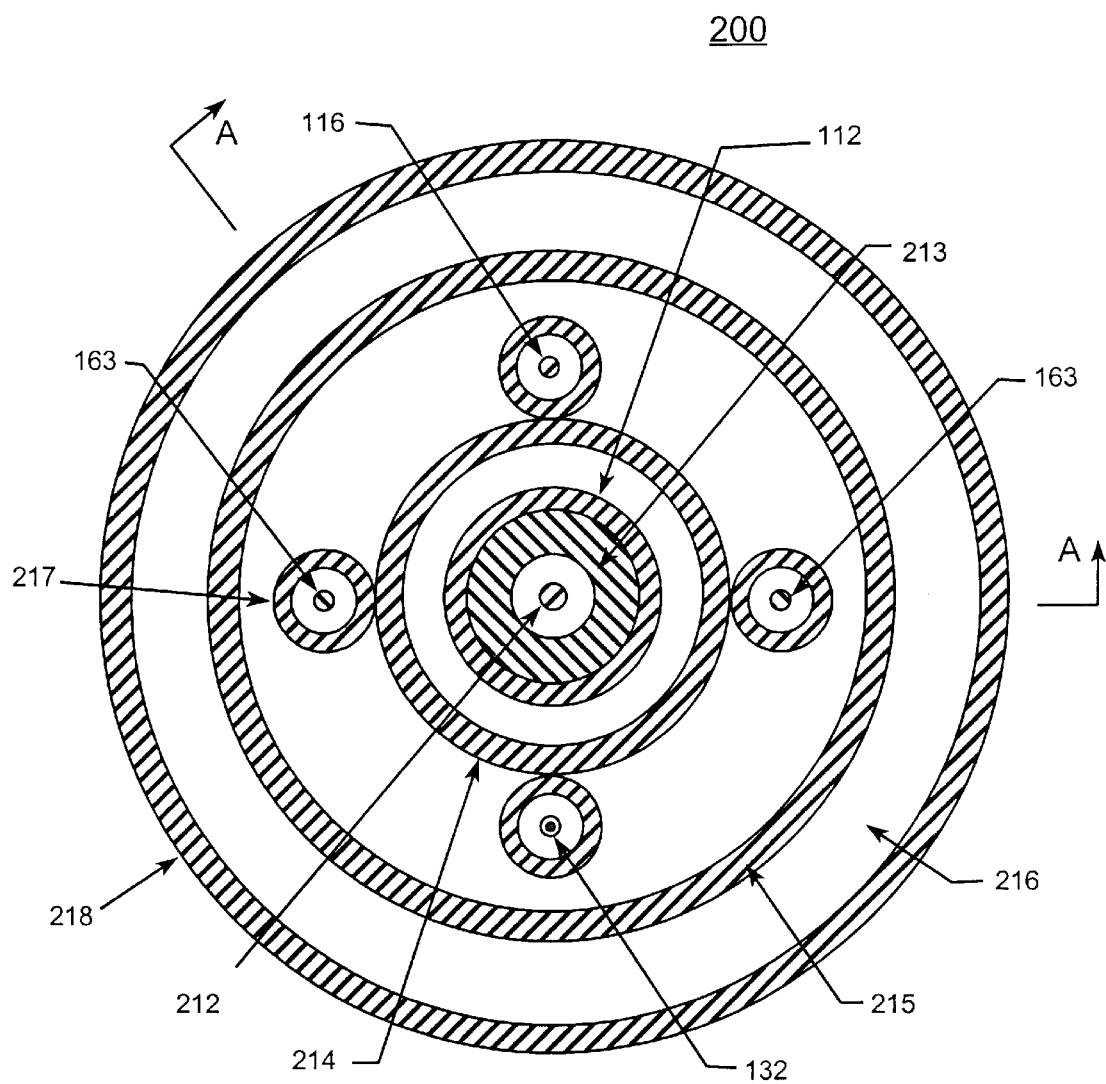
FIG. 2a is a plan view (partially in cross section) of the bottom of energy dissipating structure 200.
Figure 2B:
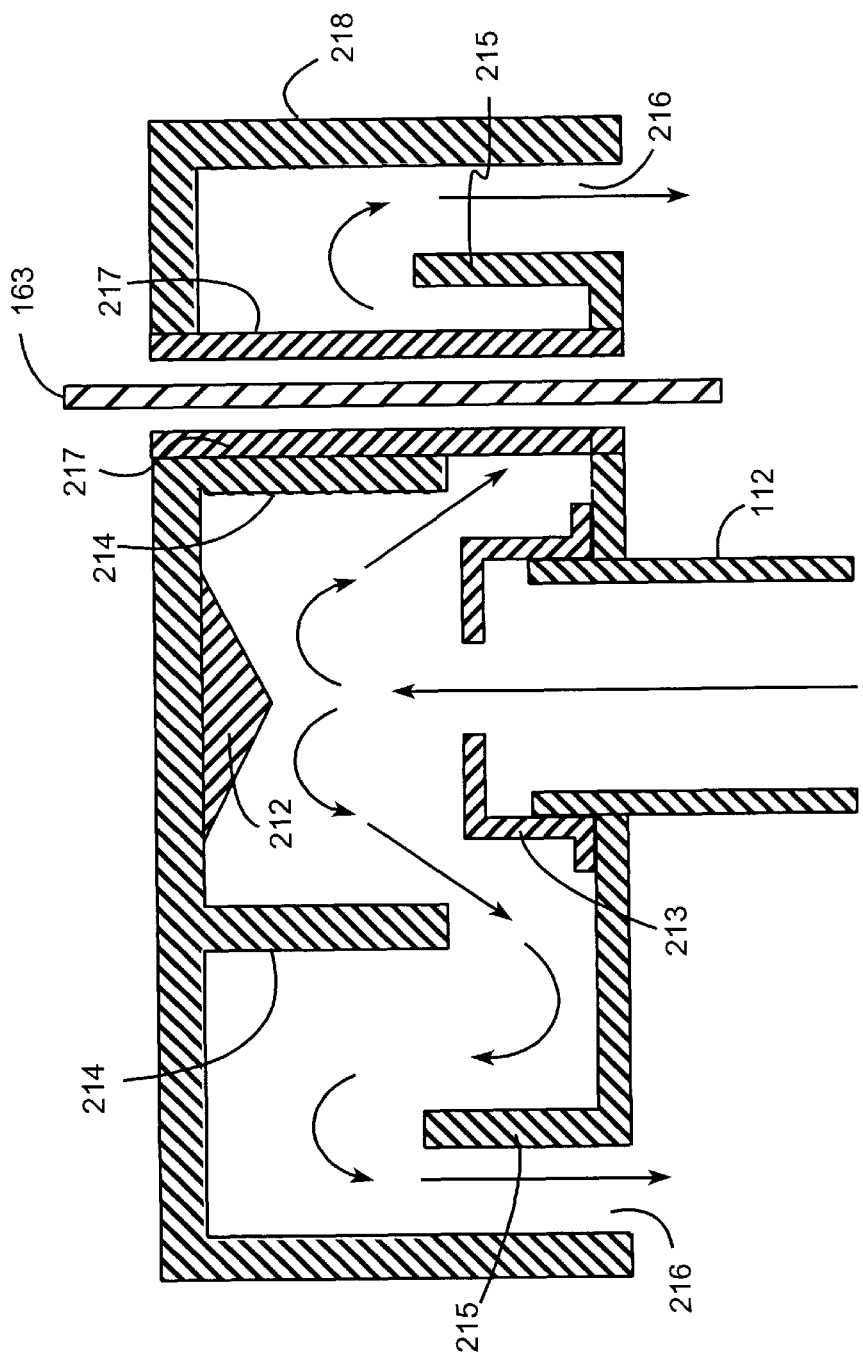
FIG. 2b is a partial sectional view (through A—A) of energy dissipating structure 200.

Referring briefly to FIGS. 2a and 2b, water flow dissipator 200 is specially designed for dissipating the high-energy unidirectional water flow entering the dissipator into a reduced-energy distributed water flow exiting the dissipator. Water exiting carrier pipe 112 is subjected to energy dissipating structures 212, 214 and 215 prior to being purged through annular-shaped opening 216 at the bottom of the water flow dissipator 200. Water flow distributor/splash guard 218 minimizes splashing around the apparatus. The various components comprising dissipating structure 200 are held together by threaded rods 163 extending through conduit 217. Conduit 217 also provides a route for electronic/power cable 132. Cable 132 (not shown in FIG. 1) connects power source 140 to programmable solenoid controller 131, data control system 121 to programming/data retrieval port 130, and programmable solenoid controller 131 to data access/programming/data retrieval port 130. A flow control orifice in compression seal cap 213 allows flow rate control through the system and also provides a watertight compression seal for holding water flow dissipator 200 on water carrier piping 112.

Referring back to FIG. 1, the carrier piping system is supported by various restraint mechanisms. The segment of piping located below support platform 155 is secured to pipe support structure 114 by pipe restraint 113. It will be obvious to one having ordinary skill in the art that myriad different mechanical restraining mechanisms could be employed for this purpose. The particular restraint employed is not critical. Pipe securing mechanism 159 is provided to positionally fix, or center, the section of carrier pipe 112 extending vertically upward from lower housing 154. In addition, securing mechanism 159 provides a stress relief function. In particular, securing mechanism 159 is designed to reduce stress which would otherwise be imparted at the interconnection of piping 112 and flow control valve 119, resulting from a forceful impact with the above-ground portion of the apparatus. Securing mechanism 159 has a collar 160 which provides a snug fit against the pipe when securing mechanism 159 is in a closed position. Securing mechanism 159 is locked into stabilizer brackets 157 with stabilizer fasteners/pins 161.

A programming/data retrieval port 130, such as a standard handset telephone jack, is integrated into the upper portion of the apparatus housing. Programming/data retrieval port 130 is adapted for receiving programming instructions from a remote hand-held programming device (not shown). For instance, the hand-held programming device could comprise a lap top computer. The hand-held electronic device communicates programming instructions (e.g., activation time) to the programmable solenoid controller. Port 130 provides for bidirectional communication between the programming device and the programmable solenoid controller 131. As a result, stored data can be downloaded from the apparatus to the hand-held electronic device for analysis. Solenoid controller 131 is provided for activating and deactivating flow control valve 119. Therefore, instructions communicated from the remote programming interface function to control the activation and deactivation of flow control valve 119, thereby controlling the purging functions of the apparatus. For instance, programmable solenoid 131 can be programmed to activate flow control valve 119 at a specific time and date, for a specified duration of time. Alternatively, chemical, electronic and/or optical sensing devices 120 provide a means for purging based on specific water parameters.

Chemical, electronic and/or optical sensing devices 120 are provided for measuring water quality parameters. In particular, the sensing devices are provided for measuring chemical and bacterial content of the water. The use of sensing devices for measuring water quality parameters is well known in the art. For instance, a water analyzing probe having a variety of sensors or electrodes for measuring various parameters of ground water is disclosed in U.S. Pat. No. 5,261,348 to Niehaus, et al. Sensing devices 120 could include pH electrodes, temperature sensors, or chlorine sensors, to name just a few. The sensing devices can be positioned at various locations within the apparatus. For instance, sensing devices 120 are positioned to test the water as it flows through carrier piping 112. Alternatively, sensing devices 120' can be mounted to the underside of separator platform 151, where they are in the path of water as it is purged from the apparatus. In this location, sensing devices 120' take advantage of the natural turbulence and scrubbing action of the flow patterns created by water flow dissipator 200, minimizing residue buildup on the sensing devices. Furthermore, sensors 120" can be configured to provide continuous water sampling by connection, via sampling tube 123, to water carrier piping 112 both before and after control valve 119. In this configuration, a minimal, continuous flow of water will exit through water flow dissipator 200. Through the power cable interconnects, a signal from sensor device 120" can be communicated to data control system 121 and programming and data retrieval port 130. Subsequently, the monitoring signal from sensor device 120" can be used by control system 121 to activate control valve 119 through the programmable solenoid controller 131.

An auxiliary water sampling feature is provided for performing manual on-site testing. The manual water sampling feature comprises water sampling tube 116 which is configured to be adapted to carrier piping 112. Tube 116 is connected to carrier piping 112 via adapter 115, positioned upstream of flow control valve 119. With flow isolation valve 118 in an open position, a portion of the water introduced into carrier piping 112 is channeled into sampling tube 116. Sampling tube 116 terminates at water sampling adapter 122. Preferably, water sampling adapter 122 is a quick connect/disconnect connector, as is well known in the art.

In the preferred embodiment of the present invention, the apparatus has electronic data control circuitry 121, including a microprocessor (not shown) for retrieving, storing, and transmitting data. Control circuitry 121 can be programmed through programming port 130 with a variety of instructions, including acceptable water parameter criteria. Programmed criteria stored by control circuitry 121 can be compared to measurement data communicated from sensing devices 120 to control circuitry 121. Control circuitry 121 has decision-making capabilities and, as a result, can signal solenoid controller 131 to activate or deactivate flow control valve 119, depending on the water quality test data.

In an alternate embodiment of the present invention, a telephone and/or radio telemetry interface control system 172 is housed in lower housing 154. These components provide a means for direct remote activation, monitoring and deactivation of the invention. The optional telemetry components can also be interfaced, either directly or indirectly, with programmable solenoid 131 to permit programming of the apparatus from remote locations.

The apparatus is powered by power source 140. Preferably, power source 140 comprises a battery, which may or may not be rechargeable. In an alternate embodiment of the present invention, at least one supplemental power source is provided. For instance, where power source 140 is a rechargeable battery, at least one solar cell 141 can be provided for recharging the battery. The optional solar cell 141 provides low-power, continuous recharging capabilities to the battery, enabling increased operating intervals between replacement or supplemental external recharging.

Furthermore, an internal water-powered turbine electric power generator 142 can be provided. Electric turbine generator 142 uses the stored kinetic energy in the pressurized water being discharged to rotate an in-line turbine, which in turn operates an electrical generator (not shown). The electrical generator is capable of meeting the electrical requirements of the invention's various electrical and electronic configurations. The turbine generator 142 is also capable of recharging optional back-up batteries or other supplemental battery power sources.

The apparatus housing has various features which will now be described. The upper portion of the housing includes access cover 150, upper housing platform 151, water flow dissipator 200, riser 153, lower housing 154, lower housing support platform 155, and lower housing cover 156.

Lower housing 154 provides a ballast effect having sufficient resistance to counter the design strength of breakaway fasteners 158. Breakaway fasteners 158 are designed to protect the expensive electronic and mechanical components of the invention. The fasteners are constructed of lower strength material than the primary connecting rods 163. As a result, the fasteners are designed to break under an extreme impact to the upper portion of the housing, allowing the connecting rods and components housed in portion 154 to escape damage from the impact.

Lower housing support platform 155 provides a buoyancy countering action in the event that the area in which the invention is installed becomes flooded. Platform 155 also provides additional weight distribution for the apparatus on the load bearing surface, minimizing the effects of settling and associated impacts. Platform 155 has a larger diameter than the remainder of the apparatus. The larger diameter platform allows for distribution of the weight of the apparatus over a greater surface area, thereby reducing the unit loading on the load bearing surface and minimizing the potential for settling.

Electrical components located in the upper portion of the apparatus are protected by an access cover 150. Access cover 150 is secured to platform 151 via locking mechanism 170, which provides keyed security. A beacon light 171 may be provided on top of access cover 150.

Platform 151 and lower housing 154 are separated by riser casing 153 and water flow dissipator 200. As assembled, dissipator 200 is positioned against the bottom side of platform 151 and riser casing 153 is positioned against the bottom of dissipator 200. Connector rods 163 are attached to collar 160 of component 159 by fasteners 162 and are locked into place by retaining pins 161. The rods 163, which extend upward through riser casing 153, water flow dissipator 200 and platform 151, are secured at a second end to the topside of platform 151 by fasteners 164.

The protective riser casing 153 is designed to permit flow dissipator 200 to discharge at an elevation that minimizes impact and erosion to the surrounding area. Protective riser casing 153 also permits the upper portion of the apparatus to be presented at an elevation that promotes easy visual identification of the apparatus.

Lower housing cover 156 may be provided with an emergency relief valve 165. In the event of a leak or other material failure in the pressurized portion of the apparatus, i.e., in lower housing 154, emergency relief valve 165 provides a means for pressure relief, thereby minimizing the potential for damage to electrical and electronic components housed in 154.

Figure 3:
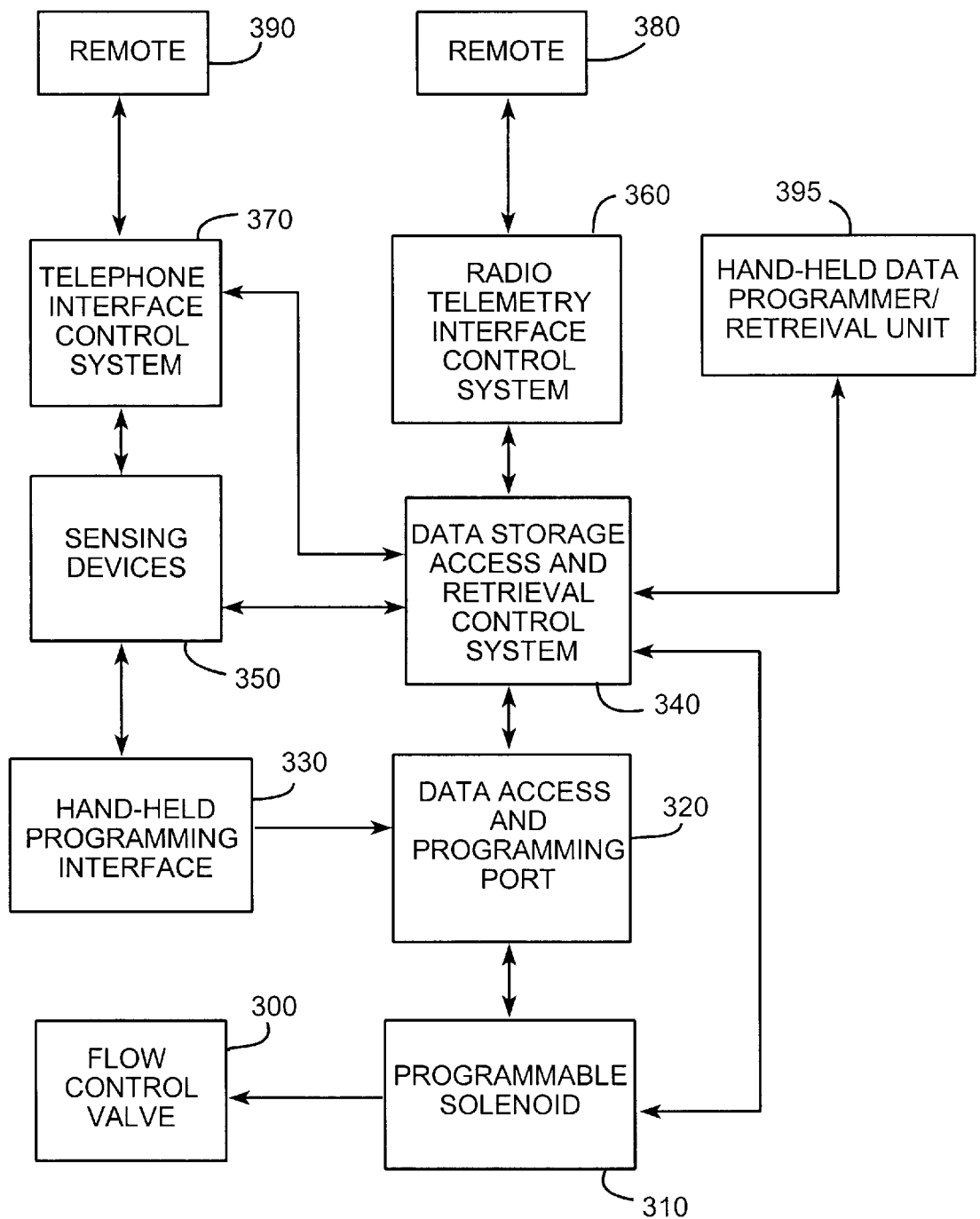
FIG. 3 is a block diagram illustrating the interaction of the major system components of the apparatus of the present invention.

Referring now to FIG. 3, although the interaction of the various components of the apparatus of the instant invention has now been described in substantial detail, a block diagram summarizing this interaction is provided. At a minimum, hand-held programming device/interface 330, programming & data retrieval port 320, programmable solenoid 310 and flow control valve 300 are provided. Operating instructions are communicated from device 330, through port 320, to programmable solenoid 310. Based upon the instructions received by solenoid 310, flow control valve 300 may be activated or deactivated for a period of time.

The preferred embodiment of the present invention further comprises central data control system 340 and sensing devices 350. In this embodiment, water quality criteria can be communicated from control system 340 to sensing devices 350, while specific water quality test data can be communicated from sensing devices 350 to control system 340. Based upon the water quality criteria and test data, control system 340 can signal programmable solenoid 310, either directly or through port 320, to activate or deactivate flow control valve 300. Hand-held programming/data retrieval unit 395, which preferably comprises a portable computer, communicates bidirectionally with data control system 340.

Optionally, telephone or radio telemetry interfaces 360, 370 can be integrated into the system of the instant invention, as a means for providing bidirectional communication with remotely operated devices 380, 390. For instance, remote devices 380 and 390 may be used to directly activate or deactivate the purging functions of the apparatus from afar, by communicating, through interfaces 360 and 370, respectively, with central control system 340.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. An apparatus for the enhancement of water quality in a subterranean pressurized water distribution system, said apparatus comprising:

a flow controlled passage for pressurized water having an inlet adapted for fluid connection to a subterranean pressurized water distribution system, said flow controlled passage having a conduit for directing pressurized water received in the inlet to an above ground routing conduit for redirecting said pressurized water downwardly toward the ground, whereby discharge of pressurized water upwardly or laterally, and associated dangers, are omitted;

a flow control valve disposed along said flow controlled passage for permitting and prohibiting the flow of pressurized water through the flow controlled passage;

programmable electronic control circuitry for controlling the flow of pressurized water through said flow controlled passage by activating and deactivating the flow control valve, said system including a programmable microprocessor system for storing instructions for activating and deactivating the flow control valve; and at least one programming interface operatively connected to the microprocessor system for inputting electronic information to be stored and processed in said microprocessor system for activating and deactivating said flow control valve.

2. The apparatus as recited in claim 1, further comprising a splash guard below said above ground routing conduit whereby erosion to the ground around said apparatus caused by said downward discharge of said pressurized water can be minimized.

3. The apparatus as recited in claim 1, further comprising at least one of chemical, electronic and optical sensing devices operatively connected to said at least one programming interface and providing data signals to the programmable electronic control circuitry, said programmable electronic control circuitry controlling said flow control valve for permitting and prohibiting said flow and discharge of said pressurized water, said flow control valve controlling flow responsive to said data signals.

4. The apparatus as recited in claim 3, wherein said at least one sensing device communicates bi-directionally with said programmable electronic control circuitry.

5. The apparatus as recited in claim 1, further comprising at least one of a telephone interface control system and a radio telemetry interface control system, said at least one interface control system for communicating bi-directionally with said programmable electronic control circuitry through said at least one programming interface.

6. The apparatus recited in claim 1, further comprising: a power source including at least one rechargeable battery; and, a supplemental power source for recharging said at least one rechargeable battery.

7. The apparatus as recited in claim 6, wherein said supplemental power source is an electronic turbine generator powered by said pressurized water.

8. The apparatus as recited in claim 6, wherein said supplemental power source is at least one solar cell for continuously recharging said at least one rechargeable battery.

9. The apparatus as recited in claim 1, wherein said above ground routing conduit is a water flow dissipator for reducing stored kinetic energy in the pressurized water and downwardly discharging the pressurized water from said apparatus.

10. The apparatus as recited in claim 1, further comprising a water sampling adapter fluidly communicating with the flow controlled passage for obtaining water samples.

11. The apparatus as recited in claim 1, wherein said flow control valve has means for adjusting the flow rate of water through said flow controlled passage.

12. The apparatus according to claim 11, further comprising a housing enclosing said microprocessor system, valve and at least a portion of said flow controlled passage for protecting against environmental factors external to the housing.

13. The apparatus of claim 1, wherein said at least one programming interface includes a port for removably interfacing with a portable programming device for programming said programmable electronic control circuitry.

14. The apparatus of claim 13, wherein the port permits bidirectional transmission of electronic information between the programmable electronic control circuitry and the portable programming device temporarily attached to the port.

15. A system for the enhancement of water quality in a subterranean pressurized water distribution system, said system comprising:

a subterranean water distribution system;

a flow controlled passage for pressurized water having an inlet adapted for fluid connection to a subterranean pressurized water distribution system, said flow controlled passage having a conduit for directing pressurized water received in the inlet to an above ground routing conduit for redirecting said pressurized water downwardly toward the ground, whereby discharge of pressurized water upwardly or laterally, and associated dangers, are omitted;

a flow control valve disposed along said flow controlled passage for permitting and prohibiting the flow of pressurized water through the flow controlled passage;

programmable electronic control circuitry for controlling the flow of pressurized water through said flow controlled passage by activating and deactivating the flow control valve, said system including a programmable microprocessor system for storing instructions for activating and deactivating the flow control valve; and, at least one programming interface operatively connected to the microprocessor for inputting electronic information to be stored and processed in said microprocessor system for activating and deactivating said flow control valve;

whereby the apparatus can purge pressurized water from a subterranean pressurized water distribution system on an automated, programmed basis to effect desired water flow in the subterranean pressurized water distribution system to control residual levels of contaminants and disinfectants in the water distribution system.

* * * * *